United States Patent [19]

Wilkinson

[11] 4,108,905
[45] Aug. 22, 1978

[54] CATALYTIC REACTIONS

[75] Inventor: Geoffrey Wilkinson, London, England

[73] Assignee: Johnson, Matthey & Co., Limited, London, England

[21] Appl. No.: 476,566

[22] Filed: Jun. 5, 1974

Related U.S. Application Data

[63] Continuation-in-part of Ser. No. 99,501, Dec. 18, 1970, abandoned.

[30] Foreign Application Priority Data

Dec. 31, 1969 [GB] United Kingdom .............. 63503/69
May 22, 1970 [GB] United Kingdom .............. 24933/70

[51] Int. Cl.$^2$ ............................................ C07C 45/02
[52] U.S. Cl. .............................. 260/604 HF; 252/472
[58] Field of Search ................................ 260/604 HF

[56] References Cited

U.S. PATENT DOCUMENTS

| | | | |
|---|---|---|---|
| 3,527,809 | 9/1970 | Pruett et al. ................. | 260/604 HR |
| 3,547,964 | 12/1970 | Olivier .......................... | 260/604 HR |
| 3,733,362 | 5/1973 | Biale ............................. | 260/604 HR |

OTHER PUBLICATIONS

Evans et al., Hydroformylation of Alkenes by Use of Rhodium Complex Catalysts, J. Chem. Soc., pp. 3133–3142 (1968).

Cotton et al., Advanced Inorganic Chemistry, Interscience Publishers, p. 791 (1966).

*Primary Examiner*—James O. Thomas, Jr.
*Assistant Examiner*—G. T. Breitenstein
*Attorney, Agent, or Firm*—Cushman, Darby & Cushman

[57] ABSTRACT

This invention relates generally to a process for the production of butyraldehyde by the catalytic hydroformylation of:

a. gaseous propylene;
b. hydrogen;
c. carbon monoxide, the hydrogen and carbon monoxide being present in a molar ratio within the range 1:15 and 2:1; and
d. a catalytically effective quantity of a hydrido carbonyl complex of rhodium which includes two phosphorus-containing stabilizing donor ligands selected from the group consisting of triphenyl phosphine and triphenylphosphite.

Specifically, the present invention concerns an improvement in the general process outlined above and consists essentially of carrying out the said reaction in the absence of any inert solvent but in the presence of a rapidly stirred liquid medium consisting of at least one of the said phosphorus containing stabilizing donor ligands in liquid form such that the ligand to complex ratio is within the range 200:1 to 5000:1 and including the steps of removing from contact with the said liquid medium a product substantially composed of gaseous butyraldehyde and condensing said product.

9 Claims, No Drawings

CATALYTIC REACTIONS

This is a continuation-in-part of application Ser. No. 99501 filed 12/18/70, now abandoned.

This invention relates to the use of rhodium complexes in catalytic hydroformylation and hydrogenation reactions and particularly to the production of butyraldehyde by the catalytic hydroformylation of propylene.

In a process for producing aldehydes by hydroformylation it has been proposed to react liquid octene-1 with hydrogen and carbon monoxide using as catalyst hydrido carbonyl tris (triphenylphosphine) rhodium in the presence of free triphenyl phosphite. The reaction takes place in the liquid phase, the octene-1 itself forming a major part of the reaction medium. It has, furthermore, been proposed to employ for the hydroformylation of hexene-1 the same hydrido carbonyl complex with free triphenylphosphine dissolved in acetophenone as solvent. The molar ratio of $H_2:CO$ in these reactions is 1:1 and high ratios of normal iso aldehyde can be achieved in these ways.

However, the rates of these reactions are relatively low and undesired paraffins are produced.

These reactions are operated as homogeneous systems in the liquid phase in the presence of an inert solvent which is nearly always an organic solvent such as an aromatic hydrocarbon or a saturated aliphatic hydrocarbon.

In the successful commercial operation of this process, however, we have found that it is essential that the reaction proceeds at a reasonable rate to give as high a yield as possible of normal (straight chain) product and that competing reactions producing hydrogenated product or iso (branched chain) product be reduced to a minimum. It is important to have free ligand to reduce the extent of hydrogenation and isomerisation reactions and to give high normal/iso aldehyde ratios.

It is believed that the rate of reaction is proportional to the catalyst concentration. We have found that processes suggested hitherto in which an inert solvent is present or in which the reactant olefin itself is a liquid and acts as solvent are obliged to have either a relatively low concentration of catalyst or a low ligand/catalyst ratio or both and, therefore, results in either a relatively low rate or low selectivity of reaction. The use of liquid olefin reactant also has a tendency to produce more of the undesired paraffin as product (by a simultaneously occurring and competing hydrogenation reaction).

It might be considered possible to overcome this low rate of reaction by the use of a relatively high partial pressure of hydrogen. We have, however, found that a high partial pressure of hydrogen has the effect of producing relatively more undesired paraffin and alcohol at the expense of aldehyde. Increasing the partial pressure of carbon monoxide whilst reducing the alcohol and paraffin production alone reduces the normal/iso ratio and reaction rates.

Similarly, increasing the temperature increases the reaction rate but decreases the normal/iso ratio.

By increasing the quantity of free stabilising donor ligand, such as triphenyl phosphine, present in the reacting solution relative to the quantity of rhodium complex present as catalyst, a partial solution to these problems can be achieved. It does, however, result in a lower rate of reaction as extra liquid solvent (either inert or in the form of olefinic reactant) is required to dissolve the extra quantity of stabilizing donor ligand. A ligand/catalyst molar ratio of 30:1 with an upper limit of 100:1 has previously been considered to be commercially the most attractive area of operation.

We have now found that a relatively high rate of reaction may be combined with favourable normal/iso ratios of product and with a low yield of undesired product such as paraffin or alcohol, by the use of a reaction system in which the reactant olefin is present as a gas and in which a liquid is used as reaction medium and from which an inert solvent is absent.

The temperature at which the reaction is carried out is relatively high, e.g. from 85° – 175° C, preferably from 115° – 140° C and most preferably from 120° – 130° C. We also prefer a relatively high ligand/catalyst molar ratio of at least 150:1 and more preferably, between 200:1 and 5000:1. The pressure at which the reaction is carried out is preferably within the range of 100 – 400 p.s.i.

With this system it is possible to use a rather lower partial pressure of hydrogen when compared with the partial pressure hitherto proposed. The system, therefore, also reduces the production of hydrogenation products.

It has previously been proposed to use molar ratios $H_2:CO$ of 1:1. We have frequently found it to be desirable to use $H_2:CO$ ratios greater than 1:3 but, on the other hand, lower $H_2:CO$ ratios may be used.

The molecular ratio $H_2:CO$ should conveniently not lie outside the range 1:15 (e.g. 1:10) to 2:1. Preferably, the $H_2:CO$ ratio is from 1:6 to 1.3.

In the absence of carbon monoxide, i.e. with hydrogen only, we have found that the present invention gives good yields of hydrogenated products. Such a system will not normally be expected to be used for a hydrogenation reaction alone as much simpler catalytic reduction systems are available. It can be used if necessary, however, and finds application where a hydroformylated olefin is required to be reduced to the corresponding alcohol (especially primary alcohol) as a one stage process:

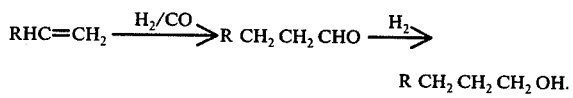

$$R\ CH_2\ CH_2\ CH_2\ OH.$$

In this way, for example, n-butanol may be obtained from propylene as an essentially one stage process.

According to this invention, there is provided a process for the production of butyraldehyde by the catalytic hydroformylation of propylene which is characterized by producing normal/iso product ratio of greater than 10:1 by reacting together:

a. gaseous propylene;
b. hydrogen;
c. carbon monoxide, the hydrogen and carbon monoxide being present in a molar ratio within the range of from 1:15 to 2:1; and
d. a catalytically effective quantity of a hydrido carbonyl complex of rhodium which includes two phosphorus-containing stabilizing donor ligands selected from the group consisting of triphenylphosphine and triphenylphosphite;

the improvement in said hydroformylation process consisting essentially of carrying out the said reaction in the absence of any inert solvent but in the presence of a rapidly stirred liquid medium consisting of at least one of the said phosphorus-containing stabilizing donor ligands in liquid form such that the ligand to complex ratio is within the range 200:1 to 5000:1 and including the steps of removing from contact with the said liquid medium a product substantially composed of gaseous butyraldehyde and condensing said product.

Included within the scope of the invention are those processes in which the molten or liquid stabilizing donor ligand used as reaction medium becomes slightly diluted with product aldehyde (or other carbonyl compound) or alcohol, as under equilibrium reaction conditions not all product may be immediately removed from the reaction zone.

It should also be understood that the stabilising donor ligand initially present in the hydrido carbonyl complex of rhodium which is used as catalyst need not be identical with the molten or liquid stabilising donor ligand which is used as reaction medium. Although it is often convenient for the same compound to be used for both purposes it is not always essential or even desirable. For example a hydroformylation catalyst such as Rh H (CO) (P Ph$_2$ Et)$_3$ (i.e. a hydrido carbonyl complex of rhodium having three ethyl diphenyl phosphine stabilising donor ligands) may be used in the presence of molten triphenyl phosphine (P Ph$_3$) as reaction medium.

The term "stabilising donor ligand" is known in the art and refers to the fact that some compounds have the power of co-ordinating with a central metal atom or ion to form a co-ordination complex in which an unusual or normally unstable oxidation state of the metal is stabilised. In this specification it is rhodium (I) which is frequently stabilised in this way.

Generally speaking suitable donor ligands for stabilisation purposes are organic compounds having in the molecule a phosphorus atom, such atom being in a valency state such that it possesses a lone pair of electrons. This valency state is normally three. Preferred ligands are often, therefore, tertiary organic phosphines or phosphites:

$R_1 R_2 R_3 P$ $(R_1O)(R_2O)(R_3O) P$ in which $R_1$, $R_2$ and $R_3$ may be the same or different and may be hydrogen, aryl or alkyl. Tri-aryl substituted phosphines such as triphenyl phosphine, trinaphthylphosphine and tri-para tolylphosphine are often preferred.

Stabilising donor ligands which may be used in this invention are often described as "biphyllic ligands". By "byphyllic ligand" is meant a compound having an element with a pair of electrons capable of forming a co-ordinate bond with a metal atom and simultaneously having the ability to accept electrons from the metal, thereby providing additional stability to the resulting complex. The term "byphyllic ligand" has been more fully defined by R. G. Pearson in Journal of the American Chemical Society, Volume 82, page 787 (1960).

The stabilising donor ligand which may be used in this invention may be a polydentate compound. This means that it may contain more than one atom which co-ordinates to the central metal atom or ion. In this invention, a stabilising donor ligand or biphyllic ligand might contain more than one phosphorus atom for example.

The complex hydridocarbonyl tris (triphenyl phosphine) rhodium (I) is stable and can be isolated. We prefer to prepare this complex separately and add it to the reaction medium before commencement of the reaction.

However, we have also found that under the conditions of the reaction, complex rhodium catalysts for use in the process according to the invention may be generated in situ in a number of different ways. For example, if the stabilising donor ligand is a tertiary organo phosphine, complex hydrido carbonyl rhodium complexes suitable for use in the present invention may be generated in situ from compounds such as:

Rh X (CO) (PR$_3$)$_3$ or

Rh X (CO) (PR$_3$)$_2$

Rh X$_3$ (PR$_3$)$_3$ where R is as stated above and X is either halogen, pseudo-halogen or a similar group. With these halogen or halogen-type complexes, an inhibition period is observed before the hydroformylation begins. We have also found that in the presence of acceptors for hydrogen halide, e.g. an organic base such as triethylamine, this inhibition period disappears. A further feature of the invention is therefore the inclusion of a compound such as an organic base which can act as a hydrogen halide acceptor in the reaction medium. Alternatively the reaction medium itself may act as an acceptor.

Hydrido carbonyl complexes of rhodium which may be used in this invention may also be generated in other ways, e.g. from rhodium compounds in other oxidation states: The rhodium can be added as a simple trivalent salt, e.g. RhCl$_3$, a rhodium carbonyl, e.g. Rh$_6$(CO)$_{16}$, a rhodium (II) carboxylate Rh$_2$(COOR)$_4$ e.g. Rhodium (II) acetate, a rhodium (I) carbonyl carboxylate e.g. [Rh(CO)$_2$ CH$_3$ COO]$_2$, rhodium sesquioxide Rh$_2$O$_3$, a rhodium (III) $\beta$ diketonate such as rhodium acetonylacetonate or a rhodium (I) carbonyl $\beta$ diketonate, e.g. Rh(CO)$_2$ (Ac ac) where Acac is acetonyl acetonate.

Particularly useful rhodium complexes which may be used as catalysts in the invention are (Ph = phenyl):

Rh H (CO)(PPh$_3$)$_3$

Rh H (CO)(PPh$_3$)$_2$

Rh H (CO)$_2$(PPh$_3$)$_2$

A particularly useful reaction medium is molten triphenyl phosphine P Ph$_3$ (m. pt. 80° C) which allows the production of a very high yield approaching virtually the maximum yield of straight chain product under the above specified conditions of reaction. With the use of this medium and in the absence of inert solvent we have obtained very good results for the hydroformylation of propylene to butyraldehyde.

In the absence of inert solvent, recovery of pure product aldehyde is a much simpler operation. In some instances, also, we have found that the use of a liquid or molten stabilising donor ligand medium has the effect of considerably extending the life of the catalyst in comparison with those systems in which inert solvent, such a hydrocarbon, is present.

The invention may be used for the hydroformylation of any olefinically unsaturated organic compound which is gaseous under the condition of the reaction. The invention has specific application in the hydroformylation of propylene, 1-butene and 1-pentene. A reduction of the isomerisation of alkenes-1 to the less desirable isomers is another advantage of the present invention.

Quite high rates of conversion per unit time per mole of catalyst present are obtained in the working of this invention and catalyst concentration in the reaction medium need not, therefore, be very high. Typical quantities are 1 - 10 millimoles of catalyst in 100 g. reaction medium. Higher or lower concentrations can, of course, be used. We have obtained good results for concentration of rhodium complex from $5 \times 10^{-3}$ to $10^{-1}$ molar concentration in the reaction medium.

Our investigations have shown that the kinetics of the chemical reaction do not appear to be adversely affected by the absence of solvent and the high concentration of ligand, whereas the rate of physical solution of the reactants is adversely affected.

The rate at which product is formed is therefore more seriously limited by the rate of physical processes than by the chemical reaction kinetics.

Higher catalyst productivity can therefore be achieved by increasing the efficiency of contact between reactants and catalyst. This is demonstrated in examples 4-12 in which increasing stirrer speed shows increasing catalyst productivity for the same set of reaction conditions.

Relatively low total pressures of hydrogen, carbon monoxide and gaseous olefinic reactant only are normally necessary.

Although we have used total pressures of 800 psi, we have found that pressures of less than 200 psi are frequently quite sufficient.

EXAMPLE 1

The following results were obtained using $10^{-3}$ moles of $RhH(CO)(PPh_3)_3$ as catalyst and a 100 fold excess of $PPh_3$, i.e. $10^{-1}$ moles in benzene as solvent. Hexene-1 concentration was 1M.

TABLE 1.

| $H_2:CO$ ratio. | Total pressure. | T° C. | % conversion in 30 min. | Straight branch chain ratio. | Loss %[1] |
|---|---|---|---|---|---|
| 1:1 | 400 psi | 65 | 77 | 4.3 | less than 3 |
| 2:1 | 400 psi | " | 63 | 5.6 | 4 approx |
| 7:1 | 800 psi | " | 52 | 5.6 | 3 (approx). |

[1]As alkane or isomerised alkene.

Using the same quantity of catalyst in 100 g of molten triphenyl phosphine i.e. a molar ligand/catalyst ratio of 380:1, with 20 ml Hexene-1 and no solvent, the following results were obtained.

TABLE 2.

| $H_2:CO$ ratio. | Total pressure psi | T° C. | % conversion in 30 min. | Straight branch chain ratio. | Loss %[1] |
|---|---|---|---|---|---|
| 2:1 | 400 | 105 | 99 | 7.2 | 15 |
| 1:1 | " | 115 | 99 | 6.0 | 24 |
| 1:1 | " | 110 | 98[2] | 6.9 | 29 |
| 1:1 | " | 85-90 | 92[3] | 16 | 7 |

[1]As alkane or isomerised alkene
[2]in 6-8 mins.
[3]in 20 min.

By comparison of tables 1 and 2 it can thus be seen that for hexene-1 in molten $PPh_3$ at 85°-90° C. there is a very high ratio of preferred product and also 92% conversion in 20 minutes or less. Using the molten medium, the other temperatures also show good results. The use of liquid olefin, however, produced rather more paraffin or isomerised alkene.

EXAMPLE 2

(a) Propylene was allowed to react with hydrogen and carbon monoxide in a closed reaction vessel in the presence of 100 g molten $PPh_3$ and $10^{-3}$ moles $RhH(CO)(PPh_3)_3$ as catalyst (i.e. a molar ligand/catalyst ratio of 380:1).

In three constituents $C_3H_6$, $H_2$ and CO were admitted to the reaction vessel, ready mixed in the molecular ratio 1:1:1. The pressure was 260 psi and the temperature 90° C.

The rate of product formation (butyraldehyde) corresponded to a pressure change of 20 psi per 3 minutes. This corresponds to 0.006 moles $C_3H_6$ converted to product per minute for $10^{-3}$ moles of catalyst. The straight branched product ratio was 12.7.

These results represent a good rate of conversion and a high yield of favourable product.

(b) In the same reaction a 1:1:1 gas mixture of propylene, hydrogen and carbon monoxide in 100 g. molten $PPh_3$ was reacted at pressures within the range 110-240 psi and temperatures from 90° - 125° C. $10^{-3}$ moles $RhH(CO)(PPh_3)_3$ were used, as before. n-butyraldehyde and isobutyraldehyde were produced at rates varying from 0.8 to 7.5 moles per mole of catalyst per minute. 94-95% of linear product was obtained. Analysis of the gas phase by gas-liquid chromatography shows that loss of alkene by hydrogenation was only about 0.3 - 0.4%. No butanol was detected.

At higher temperatures, 150° C, or above and at 110-240 psi the product ratio falls to about 6 and the rate of reaction also decreases. The catalyst decomposes at these temperatures and the $PPh_3$ medium changes colour.

EXAMPLE 3

The reaction of example 2 was repeated using the same 1:1:1 ratio of reactant gases and the same quantities of $PPh_3$ and catalyst.

Results were as follows:

TABLE 3.

| Temp. ° C. | Pressure psi | Moles aldehyde produced in 45 minutes. | Average rate (mole$^{-1}$ propylene mole$^{-1}$ catalyst min$^{-1}$) | Straight/ branched chain ratio |
|---|---|---|---|---|
| 125 | 240 | 0.338 | 7.5 | 16.01 (94.1%) |
| 90 | 240 | 0.085 | 1.89 | 9.16 (90.1%) |
| 175 | 240 | 0.185 | 4.11 | 3.38[(a)](77.2%) |

[(a)]Catalyst decomposition.

Table 3 indicates improved production of product (n-butyraldehyde) according to this invention. Preferred temperature under these conditions is 125° C (approx).

EXAMPLES 4 - 12

A series of reactions were carried out in 600 grams of molten triphenyl phosphine as reaction medium with hydrido carbonyl tris triphenylphosphine rhodium (I) present as catalyst in a stainless steel autoclave fitted with stirrer and appropriate inlet and outlet arrangements enabling the product to be continuously removed by distillation and subsequently condensed.

The products were analysed by vapour phase chromatography. Results are given in Table 4 below:

TABLE 4

| EXAMPLE | 4 | 5 | 6 | 7 | 8 | 9 | 10 | 11 | 12 |
|---|---|---|---|---|---|---|---|---|---|
| Temperature °C | 125 | 125 | 125 | 125 | 125 | 125 | 125 | 125 | 125 |
| Pressure psig | 180 | 180 | 180 | 180 | 180 | 180 | 180 | 180 | 230 |
| Triphenylphosphine present (grams) | 600 | 600 | 600 | 600 | 600 | 600 | 600 | 600 | 600 |
| RhH(CO)(PPh$_3$)$_3$ present (grams) | 0.53 | 1.4 | 1.4 | 3.5 | 3.5 | 3.5 | 3.5 | 3.5 | 3.5 |
| Molar ratio free ligand: catalyst present | 4000:1 | 1500:1 | 1500:1 | 600:1 | 600:1 | 600:1 | 600:1 | 600:1 | 600:1 |
| catalyst present Consitution of inlet gas % v/v | | | | | | | | | |
| Propylene | 68.5 | 64.4 | 63.5 | 60.9 | 65.2 | 66.6 | 67.8 | 65.3 | 65.1 |
| H$_2$ | 13.1 | 16.4 | 17.2 | 16.3 | 15.4 | 14.7 | 14.8 | 16.1 | 15.8 |
| CO | 10.9 | 12.9 | 13.4 | 12.6 | 12.3 | 12.5 | 11.6 | 12.6 | 12.7 |
| Argon[a] | 2.5 | 6.3 | 5.9 | 10.2 | 7.1 | 6.2 | 5.8 | 6.0 | 3.4 |
| Molar ratio H$_2$:CO | 1.20:1 | 1.27:1 | 1.28:1 | 1.30:1 | 1.25:1 | 1.18:1 | 1.27:1 | 1.28:1 | 1.24:1 |
| Gas inlet rates (Normal cubic feet per hour) | 7.0 | 7.0 | 7.0 | 8.0 | 7.5 | 8.3 | 9.0 | 7.0 | 11.0 |
| Stirrer speed (revs. per min.) | 420 | 420 | 420 | 420 | 420 | 1800 | 2450 | 2700 | 2700 |
| Total aldehyde produced (grams/hour) | 8.3 | 15.0 | 14.6 | 11.7 | 13.4 | 42.3 | 45.5 | 66.3 | 107 |
| grams/grm.catalyst/hour | 16.0 | 11.0 | 10.5 | 3.3 | 3.7 | 11.7 | 12.6 | 18.4 | 29.6 |
| Normal/iso ratio | 13.4 | 13.4 | 12.9 | 9.4 | 11.2 | 9.4 | 13.0 | 15.3 | 14.9 |
| % age w/w aldehyde in liquid product[b] | 99.0 | 99.5 | 99.5 | 97.5 | 99+ | 99+ | 99+ | 99+ | 99+ |
| % w/w butanol in product[c] | 0.5 | ND | ND | 2.05 | ND | ND | ND | ND | ND |

NOTES TO TABLE 4
[a]Argon was present for the purpose of calibration of the vapour phase chromatography equipment used for analysing products.[b]99+ means more than 99% of w/w.
[c]ND means not detected.

It will be noticed that with increasing stirrer speed in Examples 9 – 12 there is a considerable increase in the total quantity of aldehyde produced and in the quantity produced per unit weight of catalyst. There is also an improvement in the normal/iso ratio i.e. the quantity of desired product increases. This phenomenon is a result of the lessening of the degree of diffusion control with the better mixing produced at higher stirrer speeds. Thus, a further aspect of the invention includes the rapid stirring of the phosphorus-containing stabilizing donor ligand which comprises the liquid reaction medium.

The quite high figures for the yield of desired product per gram of catalyst per hour and the extremely favourable normal/iso ratios obtained are indicative of the advantages of this invention over the prior art processes.

Also coming within the scope of this invention are aldehydes and alcohols when produced by a method according to this invention.

Ligand/Catalyst Ratio

From the foregoing it will be understood that, in particular, we use a molten triphenyl phosphine medium and that therefore the ligand/catalyst ratio must be very high. In the foregoing Examples the ligand-/catalyst complex ratio is never less than 380:1 and in Examples 4 – 12 it ranges from 600:1 to 4000:1.

What is claimed is:

1. A process for the production of butyraldehyde by the catalytic hydroformylation of propylene which is characterized by producing normal/iso product ratio of greater than 10:1 by bringing into intimate contact the following reactants a, b, c and d at a temperature and pressure such that they react together to produce the said product;
   a. gaseous propylene;
   b. hydrogen;
   c. carbon monoxide, the hydrogen and carbon monoxide being present in a molar ratio within the range of from 1:15 to 2:1; and
   d. a catalytically effective quantity of a hydrido carbonyl complex of rhodium which includes two phosphorus-containing stabilizing donor ligands selected from the group consisting of triphenylphosphine and triphenylphosphite; the improvement in said hydroformylation process consisting essentially of carrying out the said reaction in a rapidly stirred liquid medium consisting of at least one of the said phosphorus-containing stabilizing donor ligands in liquid form, the quantity of said ligand being such that the molar ligand to complex ratio is within the range 200:1 to 5000:1 and including the steps of removing from contact with the said liquid medium a product substantially composed of gaseous butyraldehyde and condensing said product.

2. A process according to claim 1 which is carried out at a pressure between 100 and 800 p.s.i.

3. A process according to claim 2 in which the process is carried out at a pressure between 100 and 400 p.s.i.

4. A process according to claim 2 wherein the process is carried out at a pressure less than 200 p.s.i.

5. A process according to claim 2 which is carried out at a temperature between 85° and 175° C.

6. A process according to claim 5 which is carried out at a temperature between 115° and 140° C.

7. A process according to claim 1 which is carried out at a temperature between 120° and 130° C.

8. A hydroformylation process which comprises reacting together:
   a. an olefinically unsaturated compound in the form of a gas;
   b. hydrogen;

c. carbon monoxide, the hydrogen and carbon monoxide being present in a molar ratio within the range of from 1:15 to 2:1; and
d. a catalytically effective amount of a hydrido carbonyl complex of rhodium having two or more phosphorus-containing ligands selected from the group consisting of triphenylphosphine, triphenylphosphite, trinaphthylphosphine, and tri-para-tolylphosphine; the reaction being carried out in the absence of solvent but in the presence of one or more phosphorus-containing ligands in liquid form, the ligands being selected from the group consisting of triphenylphosphine, triphenylphosphite, trinaphthylphosphine and tri-para-tolylphosphine, and the ligand to complex ratio being within the range of from 150:1 to 5000:1.

9. The process of claim 8 wherein the molar ratio of hydrogen to carbon monoxide is 1:1, the olefinically unsaturated compound is an alpha-olefin, the amount of said complex is 1–10 millimoles per 100 grams reaction medium, the total pressure is between 100 and 800 psi and the temperature is between 85° and 175° C.

* * * * *